United States Patent

Daum et al.

[11] 4,137,268
[45] Jan. 30, 1979

[54] METHOD OF PREPARING AMINOACETALDEHYDE ACETALS BY THE HYDROGENATION OF DIALKOXYACETONITRILE

[75] Inventors: Gerhard Daum, Cologne; Wilhelm Vogt, Cologne-Sülz, both of Germany

[73] Assignee: Dynamit Nobel Aktiengesellschaft, Troisdorf, Germany

[21] Appl. No.: 717,789

[22] Filed: Aug. 25, 1976

[30] Foreign Application Priority Data

Aug. 28, 1975 [DE] Fed. Rep. of Germany ....... 2538231

[51] Int. Cl.² .............................................. C07C 85/12
[52] U.S. Cl. ........................... 260/584 C; 260/583 N; 260/689
[58] Field of Search ............ 260/584 R, 583 K, 584 C

[56] References Cited

U.S. PATENT DOCUMENTS

| 3,253,040 | 5/1966 | Potter et al. ..................... 260/584 C |
| 4,003,933 | 1/1977 | Drake .............................. 260/583 K |

OTHER PUBLICATIONS

Erickson et al., "JACS", vol. 77, pp. 6640–6641 (1955).

Primary Examiner—Winston A. Douglas
Assistant Examiner—John Doll

Attorney, Agent, or Firm—Sprung, Felfe, Horn, Lynch & Kramer

[57] ABSTRACT

A process for the preparation of an aminoacetaldehyde acetal of the formula

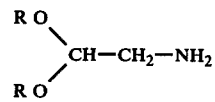

wherein
R is a saturated branched or unbranched alkyl radical of 1 to 4 carbon atomms
by contacting a dialkoxyacetonitrile of the formula

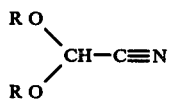

wherein
R has the same meaning with hydrogen at an elevated pressure and at a temperature of 50–180° C., preferably in the presence of a catalyst and preferably in the presence of ammonia.

8 Claims, No Drawings

METHOD OF PREPARING AMINOACETALDEHYDE ACETALS BY THE HYDROGENATION OF DIALKOXYACETONITRILE

BACKGROUND OF THE INVENTION

1. Field of the Invention

This invention relates to a process for the preparation of an aminoacetaldehyde acetal of the formula

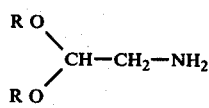

wherein
R is an alkyl radical of 1 to 4 carbon atoms by hydrogenation of the corresponding dialkoxyacetonitrile with hydrogen under an elevated pressure and at a temperature of 50°–180° C., preferably in the presence of a catalyst and preferably in the presence of ammonia.

2. Discussion of the Prior Art

It is known that aminoacetaldehyde acetals can be prepared by the reaction of halogen acetaldehyde acetals with ammonia.

According to Org. Synth. III, p. 50, aminoacetaldehyde diethyl acetal can be obtained by the reaction of chloracetaldehyde diethyl acetal and ammonia. It is disadvantageous in this process in that it is necessary to operate with a 72-fold molar excess of anhydrous ammonia. If an insufficient amount of excess ammonia is present, two molecules of halogen acetal react with ammonia to form iminodiacetaldehyde acetal. In this reaction, one mole of ammonium chloride is produced as a solid product for each mole of halogen acetal put in. In Houben-Weyl's "Methoden der Org. Chemie", Vol. VII/1, p. 381, an example is given in which 70 wt.-% of aminoacetaldehyde diethyl acetal is obtained together with 15 wt.-% of iminodiacetaldehyde diethylacetal from chloracetaldehyde acetal.

Another method of preparing aminoacetaldehyde acetals is the reaction of halogen acetaldehyde acetals with benzylamine to form benzylaminoacetaldehyde acetals and their cleavage by hydrogenation to form aminoacetaldehyde acetals and toluene. In the first stage of the reaction it is best to operate in the presence of a relatively great excess of benzylamine. The benzylamine serves also as the reaction medium and binds the halogen hydride formed in the condensation reaction. (Cf. Bristow et al., J. Chem. Soc. 1954, pp. 616–629). This known process is very difficult. Since it would not be economical to discard the benzylaminohydrochloride, an additional procedure must be used in which benzylamine is released again by a fairly strong base, such as sodium methylate for example. In this case sodium chloride precipitates and must be removed from the reaction solution by filtration or centrifugation.

Both in the first-named process and in the second, salts are produced which contain organic impurities. Before any further use, they have to be purified. A purification procedure, however, is too expensive. For environmental reasons, the contaminated salts cannot simply be discarded. Getting rid of them without polluting the environment is a difficult problem.

Accordingly, it is an object of this invention to provide a simple process for the production of an aminoacetaldehyde acetal wherein salts contaminated with organic impurities are not produced. Moreover, it is an object of this invention to provide a process for the production of an aminoacetaldehyde dimethyl acetal wherein a large excess of ammonia is not required. Especially, it is an object of this invention to provide a process for the production of an aminoacetaldehyde acetal wherein difficult to remove pollutants are not synthesized as a result of the process and the desired reaction product can readily be obtained from the reaction mixture. Especially, it is an object of this invention to provide a method for the preparation of aminoacetaldehyde acetals with the formula given above by non-polluting reactions, i.e., with reactions in which no waste products are produced whose elimination is both necessary and uneconomical.

SUMMARY OF THE INVENTION

Broadly, this invention contemplates a process for the preparation of an aminoacetaldehyde acetal of the formula

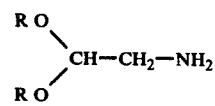

wherein
R is a $C_{1-4}$ alkyl radical, which comprises contacting a dialkoxyacetonitrile of the formula

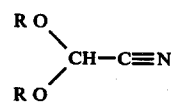

wherein
R has the meaning above, with hydrogen under elevated pressure at a temperature of 50°–180° C. Preferably, the dialkoxyacetonitrile is contacted with the hydrogen in the presence of a catalyst, especially a hydrogenation catalyst.

The process of the present invention involves the use of a dialkoxyacetonitrile reactant. The acetonitrile reactant can be formed in accordance with known procedures by the reaction of an orthoformic acid ester and hydrocyanic acid, both of which compounds are presently being produced on a large commercial scale. For example, orthoformic acid methyl and ethyl esters can be produced in accordance with German Pat. No. 2,104,206. In an analagous manner, the other orthoformic acid esters of the formula

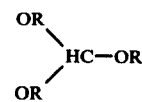

can be prepared, in which R represents saturated, branched or unbranched alkyl moieties having 3 to 4 carbon atoms. The reaction conditions are preferably chosen such that the alkali chloride formed in the reaction has little or no content of alkali alcoholate. The isolated alkali chloride can be reused without further purification, for example in alkali metal chloride electrolysis.

The dialkoxyacetonitrile reactants are prepared, in a first reaction step, by the condensation of orthoformiates with hydrocyanic acid to form dialkoxyacetonitriles. This process takes place with the splitting off of alcohol, which can be isolated by distillation and re-used. (Cf. J. G. Erikson, Journal of the American Chemical Society, 72/1338 (1951). The dialkoxyacetonitriles to be used in accordance with the invention are preferably purified by distillation before the hydrogenation.

For the achievement of optimum yields in accordance with the process, the hydrogenation is preferably effected in the temperature range of 100°–150° C. The hydrogenation is preferably performed in the presence of 2–15 moles of ammonia per mole of dialkoxyacetonitrile charged. If ammonia in liquid form is used as the only solvent, reaction temperatures around 130° C. are advantageous in the case of the preparation of the preferred product, aminoacetaldehyde dimethyl acetal.

In many cases it is desirable to perform the hydrogenation in the presence of $NH_3$ mixed with a polar organic solvent. If such solvent mixtures are used, it has proven advantageous in the preparation of aminoacetaldehyde dimethylacetal to limit the reaction temperature to a maximum of approximately 150° C.

Up to approximately 10 moles of polar solvent (in addition to ammonia) can be used for each mole of dialkoxyacetonitrile put in.

Hydrogenation in the presence of $NH_3$ has the advantage that the formation of secondary amines is largely suppressed. Optimum yields are obtained by operating in pure $NH_3$.

The hydrogen pressure can vary within wide limits. Hydrogen pressures between 1 and 300 atmospheres gauge pressure, preferably 100 to 250 atmospheres, are well suited to this special nitrile hydrogenation.

Examples of suitable polar solvents are primary low alcohols, such as methanol. But secondary alcohols, ethers, dioxane, tetrahydrofuran, dimethoxyethane and the like can also be used as polar organic solvents.

For the achievement of optimum yields it is desirable to perform the hydrogenation with a thorough exclusion of water and to use largely water-free components for the hydrogenation.

For the hydrogenation, reactors which are conventionally used for such purposes can be used, such as autoclaves equipped with magnetic stirrers, gas feeding system, pressure indicators, pressure control devices and the like. Before they are placed in operation, the reactors are flushed out with nitrogen, preferably dry nitrogen. The process of the invention is performed in the liquid phase in the presence of excess amounts of hydrogen, preferably with constant stirring of the reaction mixture. For example, the dialkoxyacetonitrile together with liquid ammonia and the catalyst are placed in an autoclave, and then, while the reaction mixture is being stirred at 20° C., hydrogen is forced in to a pressure of 150 atmospheres gauge pressure, for example. The reaction mixture is then heated to the required internal temperature of, for example, 140° C. The incipient absorption of hydrogen is indicated by the drop in the pressure. It is important to shut off the heating to prevent exceeding the maximum permissible hydrogenation temperature for the particular dialkoxyacetonitrile being used. In general the reaction is ended after about 3 to 8 hours. After the excess ammonia and hydrogen has been let off, the reaction mixture is filtered free of catalyst, and then the polar solvent that may be present is driven off. By vacuum distillation the end product is obtained in pure form. The used catalyst can be purified and regenerated for use in additional reactions.

The process of the invention can be performed continuously or discontinuously. In the case of continuous operation, one can employ known procedures which are described, for example, in Ullmanns Encyclopädie der technischen Chemie, Vol. 7, pp. 448 sqq., "Flüssigphase".

Examples of suitable catalysts are nickel or cobalt catalysts such as Raney nickel or Raney cobalt catalysts or platinum or palladium or rhodium catalysts and the like. The said metals are used preferably on a supporting material: nickel on kieselguhr, for example. The catalysts are used in amounts of 0.1 to 10 wt.-%, with respect to the dialkoxyacetonitriles used, reckoned as metal.

Surprisingly, the preparation of the aminoacetaldehyde acetals—preferably the aminoacetaldehyde dimethylacetals—is accomplished in very good yields, even though the compounds have a tendency to enter reactions in other than the desired direction. Furthermore, they are capable of entering undesired secondary reactions with the nickel catalysts used, to form, for example, complex compounds, unless the above-given reaction conditions are maintained, especially the temperatures.

Aminoacetaldehyde acetals are valuable foreproducts and intermediate products in the pharmaceutical industry. For example, they can be used in the preparation of N-heterocyclics, such as isoquinolines, for example, and the like. [Y. Org. Chem. Vol. 38, No. 9, p. SF6S (S973)]

In order to more fully illustrate the invention and the manner of practicing the same, the following examples are presented:

EXAMPLE 1

101 g = 1 mole of dimethoxyacetonitrile, 300 g of methanol, 160 ml of liquid ammonia, and 15 g of nickel catalyst G 49 A (Girdler) were placed in a one-liter autoclave. After the autoclave had been closed and the magnetic stirrer turned on, 150 atmospheres gauge pressure of hydrogen was forced in at 20° C.

Then the mixture was heated so that an internal temperature of approximately 140° C. was reached in 55 to 60 minutes, a pressure of approximately 200 atmospheres gauge being then attained. The incipient absorption of hydrogen was indicated by a drop in the pressure. It was desirable to shut off the heating so as to keep the temperature below 150° C.

After 7 hours the mixture was let cool and the autoclave was emptied after the excess hydrogen and ammonia had been carefully let out.

After the catalyst had been filtered out and the methanol had been vaporated, aminoacetaldehyde dimethylacetal was obtained in pure form by vacuum distillation.

Yield 56.7 g = 54% of the theory, $BP_{100}$: 76°–77° C.

EXAMPLE 2

202 g = 2 moles of dimethoxyacetonitrile, 160 ml of liquid ammonia and 20 g of nickel catalyst G 49 A (Girdler) were placed in a one-liter autoclave, into which hydrogen was then forced, with stirring, until the pressure had reached 200 atmospheres gauge at 20° C. The mixture was heated over a period of 25 minutes to 100° C., at which time the internal pressure reached 250 atmospheres and the hydrogenation began. By shutting off the heat, the temperature in the autoclave was kept below 122° C. until the end of the reaction. Four hours after the beginning of the experiment the mixture was let cool, the pressure was relieved from the autoclave, and the contents were rinsed out with methanol. After removal of the catalyst by filtration, the methanolic solution was analyzed by gas chromatography.

Yield of aminoacetaldehyde dimethylacetal: 151.7 g = 72.2% of the theory.

EXAMPLE 3

202 g = 2 moles of dimethoxyacetonitrile, 160 ml of liquid ammonia and 20 g of nickel catalyst G 49 A (Girdler) were placed in a one-liter autoclave and worked up as in Example 2, the experimental conditions being changed as follows:

Initial pressure: 150 atm. gauge at 20° C.

Maximum pressure: 184 atm. gauge at 118° C. after 30 min.

Maximum temperature: 131° C.

After 60 minutes the internal pressure had diminished to 100 atmospheres at 130° C.; hydrogen was again forced in until a pressure of 200 atmospheres was reached.

After a total of 315 minutes the pressure was 190 atmospheres gauge at 132° C. Since no further hydrogen absorption was taking place, the experiment was stopped. The processing of the reaction solution by distillation yielded 181.2 g of aminoacetaldehyde dimethylacetal = 86.3% of the theory, $BP_{100}$: 76°–77° C.

What is claimed is:

1. A process for preparing an aminoacetaldehyde acetal of the formula

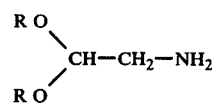

wherein
R is a $C_1$–$C_4$ alkyl radical which comprises contacting a dialkoxyacetonitrile of the formula

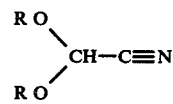

wherein
R has the meaning given above, in the presence of a solvent with hydrogen under an elevated pressure at a temperature of 50°–180° C. wherein the sole solvent is liquid ammonia.

2. A process according to claim 1 wherein the hydrogenation is effected under a pressure of 1 to 300 atmospheres gauge.

3. A process according to claim 2 wherein the hydrogenation is effected under pressure of 100 to 250 atmospheres gauge.

4. A process according to claim 1 wherein the hydrogenation is performed in the presence of 2 to 30 moles of ammonia per mole of dialkoxyacetonitrile charged.

5. A process according to claim 4 wherein the hydrogenation is performed in the presence of 2 to 15 moles of ammonia per mole of dialkoxyacetonitrile charged.

6. A process according to claim 1 wherein hydrogenation is effected in the presence of a hydrogenation catalyst.

7. A process according to claim 8 wherein the hydrogenation catalyst is a Raney nickel, Raney cobalt, platinum, palladium or rhodium hydrogenation catalyst.

8. A process according to claim 7 wherein the hydrogenation catalyst is a nickel catalyst.

* * * * *